US009073966B2

(12) United States Patent
Starkenmann et al.

(10) Patent No.: US 9,073,966 B2
(45) Date of Patent: Jul. 7, 2015

(54) INHIBITION OF SWEAT MALODOR

(75) Inventors: Christian Starkenmann, Onex (CH); Anthony Clark, Monnetier Mornex (FR); Myriam Troccaz, St-Julien-en-Genevois (FR); Yvan Niclass, Perly (CH)

(73) Assignee: Firmenich SA, Geneva (CH)

( * ) Notice: Subject to any disclaimer, the term of this patent is extended or adjusted under 35 U.S.C. 154(b) by 394 days.

(21) Appl. No.: 13/483,722

(22) Filed: May 30, 2012

(65) Prior Publication Data

US 2012/0244098 A1 Sep. 27, 2012

Related U.S. Application Data

(63) Continuation of application No. 11/779,462, filed on Jul. 18, 2007, now Pat. No. 8,206,692, which is a continuation of application No. PCT/IB2006/050098, filed on Jan. 11, 2006.

(60) Provisional application No. 60/647,777, filed on Jan. 31, 2005.

(30) Foreign Application Priority Data

Jan. 31, 2005  (EP) .................................... 05100619

(51) Int. Cl.
| | | |
|---|---|---|
| *C12Q 1/02* | (2006.01) | |
| *A61K 8/00* | (2006.01) | |
| *C07K 5/062* | (2006.01) | |
| *C07C 237/12* | (2006.01) | |
| *C07C 237/16* | (2006.01) | |
| *C07K 5/02* | (2006.01) | |
| *C12Q 1/527* | (2006.01) | |

(52) U.S. Cl.
CPC ........... *C07K 5/06026* (2013.01); *C07C 237/12* (2013.01); *C07C 237/16* (2013.01); *C07K 5/0215* (2013.01); *C07K 5/0606* (2013.01); *C07K 5/06069* (2013.01); *C12Q 1/025* (2013.01); *C12Q 1/527* (2013.01); *G01N 2500/00* (2013.01)

(58) Field of Classification Search
None
See application file for complete search history.

(56) References Cited

U.S. PATENT DOCUMENTS

| 2,542,767 A | 2/1951 | Gresham et al. .............. 560/175 |
| 5,104,929 A | 4/1992 | Bilkadi ........................ 524/847 |
| 5,213,791 A | 5/1993 | Lyon et al. ....................... 424/65 |
| 2001/0041789 A1 * | 11/2001 | Nagasawa ..................... 530/331 |
| 2002/0159997 A1 * | 10/2002 | Patti et al. .................. 424/142.1 |
| 2004/0241795 A1 | 12/2004 | Natsch et al. ................ 435/69.1 |

FOREIGN PATENT DOCUMENTS

| EP | 0 815 833 B1 | 1/1998 |
| WO | WO 02/092024 A2 | 11/2002 |
| WO | WO 2004/031766 A1 | 4/2004 |

OTHER PUBLICATIONS

International Search Report, application No. PCT/IB2006/050098, mailed Sep. 8, 2006.
Diamond et al., "Reversing the Amino Acid Sequence of a Dipeptide Changes its Partition in an Aqueous Two-Phase System," Biotechnology Techniques, 3(4):271-274 (Jul./Aug. 1989).
Hasegawa et al., "Identification of new Odoriferous Compounds in Human Axillary Sweat," Chemistry & Biodiversity, 1(12):2042-2050 (Dec. 2004).
Hendriks et al., "Isolation and characterisation of renal metabolites of γ-glutamylfelinylglycine in the urine of the domestic cat (*Felis catus*)," Comparative Biochemistry and Physiology, Part B: Biochemistry and Molecular Biology, 139(2):245-251 (Oct. 2004).
Kasuya et al., "Glycine Conjugation of the Substituted Benzoic Acids in Mice: Structure-Metabolism Relationship Study II," Journal of Pharmacobio-Dynamics, 14(12):671-677 (Dec. 1991).
Katz et al., "Formation of Propionyl-, Butyryl-, and other Acylglycines by Enzymes of *Clostridium kluyveri*," The Journal of Biological Chemistry, 200(1):431-441 (Jan. 1953).
Loring et al., "The Synthesis of Crystalline Cystinyldiglycine and Benzylcysteinylglycine and their Isolation from Glutathione," The Journal of Biological Chemistry, 111:385-392 (Oct. 1935).
Natsch et al., "Identification of Odoriferous Sulfanylalkanols in Human Axilla Secretions and their Formation through Cleavage of Cysteine Precursors by a C-S Lyase Isolated from Axilla Bacteria," Chemistry & Biodiversity, 1:1058-1072 (Jul. 2004).
Starkenmann et al., "Identification of the Precursor of (*S*)-3-Methyl-3-sulfanylhexan-1-ol, the Sulfury Malodour of Human Axilla Sweat," Chemistry & Biodiversity, 2(6):705-716 (Jun. 2005).
Troccaz et al., "3-Methyl-3-sulfanylhexan-1-ol as a Major Descriptor for the Human Axilla-Sweat Odour Profile," Chemistry & Biodiversity, 1(7):1022-1035 (Jul. 2004).

* cited by examiner

*Primary Examiner* — Sue Liu
*Assistant Examiner* — Thor Nielsen
(74) *Attorney, Agent, or Firm* — Winston & Strawn LLP (57) ABSTRACT

The present invention relates to a method for screening compounds having the ability to prevent, suppress or reduce malodor development on body surfaces. In particular, the method allows to efficiently screen for compound having the ability of preventing sweat malodor development caused by volatile sulfur compounds (VSCs). The present invention is based on the finding of the direct precursor of naturally VSCs, which is present in human sweat and which will be metabolized by Staphylococci to VSCs.

10 Claims, 5 Drawing Sheets

INHIBITION OF SWEAT MALODOR

CROSS-REFERENCE TO RELATED APPLICATIONS

This application is a continuation of U.S. application Ser. No. 11/779,462, filed Jul. 18, 2007, which is a continuation of International application PCT/IB2006/050098 filed Jan. 11, 2006, which claims the benefit of U.S. provisional application 60/647,777 filed Jan. 31, 2005. The entire content of each prior application is expressly incorporated herein by reference thereto.

TECHNICAL FIELD

The present invention relates to a method for screening compounds having the ability to prevent, suppress or reduce malodor development on body surfaces. The present invention also relates to a compound of formula (I), which is a precursor of malodorous volatile sulfur compounds. In addition, the present invention relates to methods for preventing malodor and to methods for preparing products having the ability to reduce malodor development.

BACKGROUND

The prevention of axillary malodor is a constant objective of scientific endeavor. It has been recognized for some time that sweat itself, as it is excreted from apocrine sweat gland abundantly present in the underarm skin, is generally odorless. Axillary malodor essentially develops upon the metabolic activity of certain strains of bacteria that have evolved to live in this niche environment and which are well adapted to growing on the peculiar cocktail of odorless precursors found in apocrine sweat.

Several classes of malodorous substances have been isolated so far, one class is from steroidic origin, another class encompasses bacterial degradation compounds: short chain fatty acids like (E/Z)-3-methyl-2-hexenoic acid, described as predominant olfactory contributor of the sweat malodor.

A third class of sulfur compounds has only very recently been discovered and has been disclosed independently in WO 200403766, in Troccaz et al., "3-Methyl-3-sulfanylhexan-1-ol as a Major Descriptor for the Human Axilla-Sweat Odor Profile" Chemistry & Biodiversity, Vol. 1 (2004); and in Natsch et al., "Identification of Odoriferous Sulfanylalkanols in Human Axilla Secretions and Their Formation through Cleavage of Cysteine Precursors by a C—S Lyase Isolated from Axilla Bacteria", Chemistry & Biodiversity, Vol. 1 (2004).

One particularly malodorous specimen of the class of sulfur compounds was found to be 3-methyl-3-sulfanylhexan-1-ol (Troccaz et al., followed by Natsch et al. and Hasegawa et al. "Identification of New Odoriferous Compounds in Human Axillary Sweat" Chemistry and Biodiversity Vol. 1 (2004) 2042-50). The same compound is also disclosed in U.S. Pat. No. 6,610,346, where it is used as a flavor in foods and beverages for providing cooked vegetable (onion) and meaty notes to food products.

Presently, malodor development has been tackled in different ways, for example by applying anti-bacterial substances to the axillary skin, by providing perfume compositions capable of masking malodor, by trapping malodorous molecules, for example by applying cyclodextrin, for inhibiting β-lyases, for example.

With the objective to prevent the formation of volatile sulfur compounds (VSCs) as, for example, S-3-methyl-3-sulfanylhexan-1-ol it becomes indispensable to elucidate its metabolic pathway, and, in particular, its direct precursor. Such insight would allow designing screening for compounds having the ability of intervening in the pathway and thus inhibit the formation of the VSC.

Accordingly, Natsch et al. have speculated that the cysteine conjugate of VSCs (Cys-S-3-methyl-3-sulfanylhexan-1-ol), was the direct precursor for VSCs and that, cleavage of the precursor by a C—S β-lyase present in *Corynebacterium* spp. would directly yield the VSC.

Similarly, Lyon et al. (U.S. Pat. No. 5,213,791), disclosing amino acid β-lyase inhibitors as deodorants, considered that the Cys-S-conjugate was the most relevant precursor on col. 2, line 5-6. These findings corresponds to the well-reported pathway of thiols and thiolmethyl metabolites starting with glutathione conjugates, which undergoes sequential enzymatic hydrolysis to yield the thioether of cysteine.

A further objective of the present invention is to identify the bacterial species or strains, which are able to convert non-odoriferous precursors of human sweat into malodorous VSCs, allowing to more precisely targeting the origin of malodor development.

Accordingly, Natsch et al. concluded that non-odoriferous precursors of axillary secretions are transformed into volatile substances by bacterial enzymes present only in *Corynebacterium* spp. and not in staphylococci.

In view of the prior art, the objective of the present invention is to find other, direct precursors of volatile sulfur compounds responsible for axillary malodor. It is a further objective to identify further bacterial strains responsible of producing volatile sulfur compounds. The knowledge on precursors and bacterial strains at the origin of malodorous compounds may then be used to more effectively combat axillary malodor development in humans, for example by providing effective screening methods for compounds inhibiting the formation of VSCs. Therefore, it is a further objective of the present invention to provide new methods or ways for preventing development of malodor.

SUMMARY OF THE INVENTION

The inventors of the present invention surprisingly found that the direct precursor of volatile sulfur compounds (VSCs) is the S-conjugate of Cysteine-Glycine, and that the Cysteine conjugate reported from the prior art was a clearly less efficient precursor of VSCs. In further contrast to current prior art teaching, strains of *Staphylococcus haemolyticus* are able to convert the Cys-Gly conjugate into VSCs with higher efficiency than *Corynebacterium* and *St. epidermidis* strains, all of which found in human axillae.

Accordingly, the present invention provides, in a first aspect, a method for screening compounds having the ability to prevent, suppress or reduce malodor development on body surfaces, the method comprising the steps of providing a medium comprising a compound to be screened, adding to the medium at least one precursor compound of the formula (I), determining the increase of at least one metabolite of the precursor, and/or the disappearance of the precursor, and, concluding, from the ability of the compound to prevent increase of a metabolite of the precursor, or to prevent disappearance of the precursors, the compound's ability to prevent or suppress malodor development.

In a second aspect, the present invention provides a compound of formula (I)

(I)

in which:

—Y defines a leaving function and —$R_1$ represents a $C_1$-$C_{20}$ residue for an active compound of the formula HY—$R_1$, or, in which —Y—$R_1$ is OH or SH, and, the dotted line represents a double bond, in case of which X is selected from $CR_4$, and N, or, the dotted line represents a single bond, in case of which X is selected from $NR_4$, $CR_4R_5$, O and S, with $R_4$ and $R_5$ being, independently of each other, selected from H and $C_1$-$C_{10}$ alkyl, alkenyl or alkynyl residues.

In a third aspect, the present invention provides the use of bacteria of the family Staphylococci in screening methods, assays or research methods of body malodor development, inhibition, and/or occurrence. Correspondingly, the present invention provides a method for elucidating body malodor development, the method comprising the step of applying Staphylococci, or an enzyme derived from it, to a malodor precursor compound.

In a forth aspect, the present invention provides the micro-organisms *Staphylococcus haemolyticus* and *St. epidermidis* with CNCM deposit numbers 1-3357 and 1-3356, respectively.

In a fifth aspect, the present invention provides a method for preventing sweat malodor, the method comprising the step of applying to a body surface, preferably to the axillary skin, a compound capable of inhibiting the conversion of the compound of formula (I) with X=NH, the dotted line being a single bond, Y=S and $R_1$ being a $C_4$-$C_{10}$ alkyl residue carrying a hydroxyl group to a volatile sulfur compound.

In a sixth aspect, the present invention provides a method for preparing a product having the ability to reduce malodor development, comprising the step of adding to the product a compound capable of inhibiting the conversion of the compound of formula (I) as defined in above (fifth aspect) to a VSC.

In a further aspect, the present invention provides a method for metabolizing a compound of the formula (I) under controlled conditions, the method comprising the step of exposing the compound of formula (I) to a micro-organism and/or to a β-lyase.

In a still further aspect, the present invention provides a compound of formula (III) given below.

DETAILED DESCRIPTION OF THE PREFERRED EMBODIMENTS

Within the context of this specification the word "comprises" is taken to mean "includes, among other things". It is not intended to be construed as "consists only of".

In the context of the present invention, percentages are percentages by weight of dry matter, unless otherwise indicated. Similarly, if proportions are indicated as parts, parts of weight of dry matter are meant.

The present invention provides a precursor compound of the formula (I)

(I)

in which:

—Y defines a leaving function and —$R_1$ represents a $C_1$-$C_{20}$ residue for an active compound of the formula HY—$R_1$, or, in which —Y—$R_1$ is OH or SH, and, the dotted line represents a double bond, in case of which X is selected from $CR_4$, and N, or, the dotted line represents a single bond, in case of which X is selected from $NR_4$, $CR_4R_5$, O and S, with $R_4$ and $R_5$ being, independently of each other, selected from H and $C_1$-$C_{10}$ alkyl, alkenyl and alkynyl residues.

The term active compound for HY—$R_1$ refers to an organic compound, which may be used in screening methods. For example, it is a compound that can be easily detected. Preferably, HY—$R_1$ is an odorant compound. Alternatively, HY—$R_1$ may be a fluorescent compound. Generally, HY—$R_1$ may be a compound that has the quality of a marker, for example in that it has different physical or chemical properties than the compound of formula (I), which can easily be quantified, for example by absorbance or fluorescence, for example. Quantification may generally be made by spectrophotometric assays for high-throughput screening.

Preferably, the leaving function —Y— is selected from the group of S, O, $NR_2$, $N^+R_2R_3$, OCO. If —Y— is $N^tR_2R_3$, $R_1$ preferably carries a negative charge.

More preferably —Y— is selected from S and O, most preferably it is S.

In an embodiment of the present invention, $R_1$ is a $C_1$-$C_{20}$ alkyl, alkenyl or alkynyl compound, optionally carrying one or more functional groups selected from hydroxy, carbonyl, carboxyl, amino, amid groups and halogen atoms.

More preferably, $R_1$ is a $C_3$-$C_{16}$ organic residue, more preferably it is a $C_5$-$C_{10}$ organic residue.

Preferably, $R_1$ is a $C_3$-$C_{16}$ organic alkyl or alkenyl carrying at least on functional group selected from a hydroxy, carbonyl, carboxyl group. More preferably, $R_1$ carries a hydroxy group.

Figure 2:
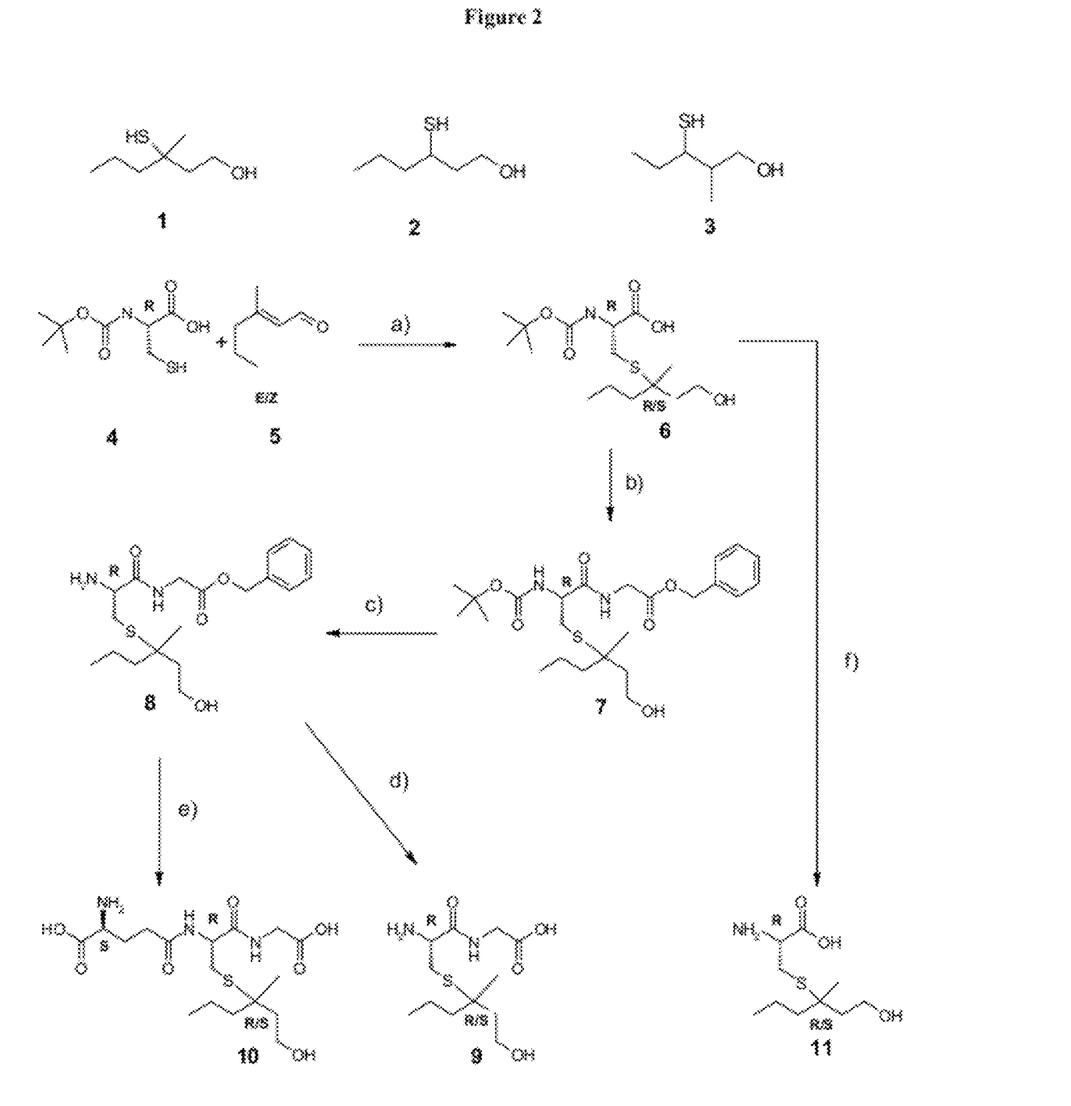
FIG. 2 shows malodorous volatile sulfur compounds (1, 2, 3) and putative precursor compounds (9, 10, 11), compound 9 of which turned out to be the most efficient precursor for compound 1. Arrows indicate the steps of synthesis of precursors.

Preferably, $R_1$ is selected from the group consisting of the compounds:

The precursors with the above residues $R_1$=1', 2', or 3' and Y=S will release, upon enzymatic activity, corresponding VSCs (1), (2), (3), see FIG. 2. Respectively, precursors with residues (12') and (13') will release VSC in which the dotted line is replaced by a —S bond.

Preferably, the dotted line in formulae (I) represents a single bond with X selected from O, S, $NR_4$, $CR_4R_5$, with $R_4$ and $R_5$ being defined as in formula (I) above, and with Y being selected from S and O. More preferably, X is selected from NH and $CH_2$. Most preferably X is NH and Y is S.

Preferably, in the compound of formula (I) above, the dotted line represents a single bond, Y is selected from O and $S_1$ and $R_1$ is a $C_3$-$C_{16}$ alkyl carrying one or more functional groups selected from a hydroxy, carboxy and carbonyl group.

Therefore, in a preferred embodiment, the precursor compound of formula (I) corresponds to the compound of formula (I') below in which $R_1$ is as defined above for the compound of formula (I).

Compound (I'), together with the residues $R_1$=(1'), (2'), (3'), (4'), (12'), or (13') corresponds to the most efficient precursor of VSCs found in axillary sweat, as the present inventors have established. On the basis of this surprising finding, an effective screening method can be established.

A preferred embodiment of the precursor can be synthesized following the scheme given in FIG. 2. Generally, in a first step, N protected cysteine (N-Boc) may be added by 1,4-addition to an α,β-unsaturated aldehyde. The aldehyde structure is preferably related to the corresponding VSC as disclosed by Natsch et al (2004), scheme 1. Accordingly, if hex-2-enal is selected as the starting α,β-unsaturated aldehyde, a precursor of formula (I) with R=(2') above is obtained. In a similar way, In order to obtain a precursor with R=(1'), the precursor is synthesized from 3-methyl-hex-2-enal. The cysconjugate may be directly obtained after deprotection with TFA (trifluoroacetic acid), preferably in an appropriate solvent, for example $CH_2Cl_2$.

In a further step, Glycine may be coupled to the protected Cysteine conjugate obtained above (for example, Boc-L-Cys-conjugate). This step may be performed with H-Gly-OBz (Bz=—$CH_2$—$C_6H_5$) in $CH_2Cl_2$ in the presence of Benzotriazol-1-yl-oxytripyrridolidino-phosphonium (PyBOP) and diisopropylamine (DIPEA) in standard conditions for peptide synthesis (Troccaz et al. (2004)).

In a further step, the α-amino-protecting group may be removed, for example in $CH_2Cl_2$ and TFA conditions.

In a still further step, the benzoyl protective group may be removed by saponification in water, ethanol and sodium hydroxide 2%, for example, in order to obtain compounds of the formula (I).

The precursors according to the present invention will, upon cleavage of the C—Y bond, release compound of formula (II) given below in which $R_1$ and Y are defined as above for the compound of formula (I).

Preferably, compound (II) is a malodorous VSC, of the formula SH—$R_2$. The synthesis of compounds of this formula has been disclosed by Troccaz et al. (2004), which is totally incorporated herein by reference.

The method of screening of the present invention has the purpose of determining in an efficient manner if a particular compound has the ability to prevent, suppress or reduce malodor development on body surfaces. In particular, the malodor development on body surfaces refers to malodors linked to excretions of humans and animal sweat glands. On bodily surfaces, and especially in the axillae of humans, these excretions are exposed to a diverse flora of micro-organisms that metabolize non-odoriferous precursors into volatile compounds generally regarded as malodorous or displeasing. Therefore, the term bodily surfaces generally refers to parts of skin containing sweat excreting glands, and especially to the human underarm region. The ability of preventing, suppressing or reducing refers to the ability of a given compound to inhibit in any way the occurrence of malodor. For example, this ability may consist of simply stopping the further release of malodor having already strongly developed, or it may prevent malodor from the beginning, for example.

The term malodor refers generally to malodor associated with volatile compounds produced upon microbial activity on sweat. Preferably, in the context of the present invention, the term malodor refers to the odors of volatile sulfur compounds (VSCs), which is generally regarded as unpleasant.

The method for screening of the present invention comprises the step of providing a medium comprising a compound to be screened.

Principally, the medium may be any liquid in which enzymatic reaction can take place. For example, the medium can simply consist of liquid sweat collected from human or animal individuals. More practically, the medium is an aqueous solution, optionally comprising buffers and/or nutrients supporting a quick metabolic activity of the enzymes or biological systems of the screening method.

Depending on the way the enzymatic reaction is controlled, a suitable medium may be selected. For example, if the enzymatic reaction is designed to be performed by a micro-organism, a medium allowing viability or even growth of the micro-organism is to be selected. Phosphate buffer, for example, allows survival of micro-organisms but does not contain any further nutrient and is thus a preferred medium for the screening method of the present invention. Preferably, 0.001-1 M, more preferably 0.05-0.5 M phosphate buffer is used.

Preferably, the pH of the medium is in the range of 3-9, more preferably 4-8, most preferably 5-7.5.

If, on the other hand, an isolated enzyme for catalyzing the enzymatic reaction, the medium may be selected or adjusted to allow for optimized enzymatic activity in dependence of the enzyme preferences. Typical variables for adjusting a solution to the optimal conditions for an enzyme include, temperature, pH, presence or absence of salts, BSA, buffering agents, EDTA, and others, for example.

A compound to be screened is added to the medium. The compound to be screened for its ability to prevent development of malodor may be randomly selected by the skilled person, or it may be selected according to structural criteria, for example. Known inhibitors of β-lyases are preferred candidates of compounds to be screened. Surprisingly, however, *Staphylococcus* is not reported to have a β-lyase having significant similarity to known β-lyases, and other compounds may thus prove to be efficient inhibitors.

In an embodiment of the present invention, the compound to be screened is a compound of the formula (III) below:

(III)

in which:

$R_6$ is a $C_2$-$C_{20}$, linear, branched or cyclic alkyl, alkenyl, alkynyl or aryl residue, optionally substituted and optionally comprising one or more heteroatoms, and, the dotted line represents a double bond, in case of which Z is selected from $CR_7$, and N, or, the dotted line represents a single bond, in case of which Z is selected from $NR_7$, $CR_7R_8$, O and S, with $R_7$ and $R_8$ being, independently of each other, selected from H and $C_1$-$C_{10}$ alkyl, alkenyl and alkynyl residues.

Preferably, $R_6$, if substituted, is substituted with a $C_1$-$C_{10}$, linear, branched or cyclic alkyl, alkenyl, alkynyl or aryl residue, optionally comprising one or more heteroatoms. More preferably, $R_6$, if substituted, is substituted with an alkyl, alkoxyl, amine, alcohol, thiol, carboxyl, and/or hydroxylamine, for example.

Preferably, the at least one heteroatom is selected from N, O, S, F, Cl, Br, I.

Preferably, $R_6$ carries at least one amino group.

Preferably, $R_6$ is a $C_2$-$C_{10}$ linear, branched or cyclic alkyl, alkenyl, alkynyl or aryl residue, optionally comprising one or more heteroatoms.

Preferably, $R_6$ is an optionally substituted 5 or 6-membered ring optionally comprising a heteroatom selected from O, N and S. More preferably, $R_6$ is a 5- or 6-membered ring comprising S.

Preferably, $R_6$ comprises a 5-membered ring substituted with at least one amino group. According to a preferred embodiment, the compound to be screened has the formula (IIIa)

(IIIa)

Preferably, $R_6$ is a linear or branched oxime. In this case the compound to be screened may have the formula (IV)

(IV)

where $R_9$ is hydrogen, phenyl or $C_1$-$C_8$ alkyl which is unsubstituted or substituted by a phenyl group, a hydroxy group, a carboxy group, a benzyloxy group or benzyloxycarbonyl group, a halogen atom or an amino group, and where Z and the dotted line are defined as in formula (III) above.

Alternatively, $R_6$ may be a branched $C_2$-$C_{10}$ compound, wherein one branch carries an amino group. For example, the other branch is selected from an alkenyl or alkynyl. As another example, one branch carries an amino group and the other branch is an alkyl halogenide. Preferably, it is an alkyl halogenide with the halogen selected from Cl, Br, and As a still other example, the other branch carries an alkyl-, alkenyl, or alkenyl sulfonyl group.

For example, the compound to be screened may be selected from the compound of the formula (V) given below:

(V)

in which Z is defined as above for compound (III), and $R_8$ is selected from the group consisting of a $C_2$-$C_5$ alkenyl or alkynyl, a $C_1$-$C_5$ alkyl, alkenyl or alkynyl halogenide, and, an alkyl sulfonyl of the formula —O—$SO_3$—$R_9$, with $R_9$ being selected from a $C_1$-$C_5$ alkyl, alkenyl or alkynyl residue.

Preferably, the dotted line in formulae (III), (IV) and (V) represents a single bond. Preferably, Z is selected from $NR_7$,

$CR_7R_8$, with $R_7$ and $R_8$ being defined as in formula (III) above. More preferably, Z is selected from NH and $CH_2$. Most preferably it is NH.

Preferably, $R_8$ in formula (V) is a $C_2$-$C_5$ alkynyl. More preferably it is 2-propynyl, providing formula (VI) below:

(VI)

Alternatively, the compound to be screened may be (VII)

with Z being defined as in the paragraph above. Upon screening of compound (VII) with z being NH it was found, very surprisingly, that this compound actually did not inhibit the formation of metabolites like compound II, but, on the contrary, did result in an clear and confirmed increase of metabolites. This makes compound (VII) a useful compound for increasing malodor production. Compound VII is thus useful as a modulator of production of volatile compounds on body surfaces or in vitro, for example for testing potentially inhibiting compounds under more severe conditions in the screening method of the present invention.

The screening method of the present invention comprises the step of adding to the medium at least one precursor compound. The precursor may be selected from the compounds of formula (I) given above.

In an embodiment, the screening method of the present invention further comprises the steps of adding to the medium at least one bacterial strain selected from the taxa staphylococci, *corynebacteria* and bacilli, or a preparation comprising a functional β-lyase. Preferably, the strain is selected from the bacterial family of *Staphylococcus* spp. and/or *Corynebacterium* spp. Preferably, the bacterial strain is selected from the bacterial family of Staphylococci. More preferably the strain is selected from the group consisting of *St. epidermidis*, *St. haemolyticus*, *St. capitis* and *St. homidis*. Even more preferably, the bacterial strain is selected from *St. haemolyticus* and *St. epidermidis*. Most preferably, the bacterial strain is selected from *St. epidermidis* with deposit number CNCM I-3357 and *St. haemolyticus* CNCM I-3356.

As has been mentioned above, the present inventors surprisingly found that *Staphylococcus* strains colonizing the human underarm region efficiently release VSCs. The prior art is so far silent on this subjects and the strains of *Staphylococcus* are thus preferably used in the screening method of the present invention. On the other hand, the present inventors have also shown that *Corynebacterium* strains efficiently metabolize the novel precursor the compound of formula (I) and may thus nearly equivalently be used in the screening method of the present invention.

Preferably, the micro-organism, before addition to the medium of the screening method, is grown in a nutritive medium. For example, for micro-organisms of the genders *Staphylococcus* or *Corynebacterium*, a Mueller-Hinton Broth (Difco) or a Triptic soya broth (Difco) may be used, preferably supplemented with 0.005 to 0.5% Tween 80, for example.

Preferably, the micro-organism, before adding it to the medium of the screening method, is cultivated in the growing medium until growth is exponentially increasing and/or until increase of biomass per time is maximal. Preferably, the growing medium comprises $10^{0.5}$-$10^{14}$ cfu/ml at this stage. Thereafter, it may be removed from the growing medium, optionally washed, and added to the medium of the screening method. The latter preferably has low or no nutrients other than the precursor of the present invention, thus inciting the micro-organism to metabolize the precursor.

Alternatively, the micro-organism may be replaced or supplemented by the functional enzyme capable of cleaving the precursor into the malodorous substance. The enzyme may originate from an enzyme preparation on the base of micro-organisms, for example, or it may be an isolated enzyme. The isolated enzyme may be obtained by genetic engineering and/or biotechnology.

The concentration of the constituents of the screening method of the present invention is preferably adapted to levels that permit quantification by standard analytical methods, for example. Since VSCs potentially released from the precursor generally are detectable by the human nose at low concentrations, the corresponding precursors can be used in correspondingly low concentrations.

Generally, the compound to be screened is added at least at equal or at higher concentrations than the precursor.

As an example, the medium of the screening method preferably comprises 2-500, preferably 3-200, most preferably 4-100 μmol/L, of the compound to be screened. Preferably, the precursor is added in amounts in generally the same ranges as indicated for the compound to be screened above. At the skilled persons discretion, the ratio of the compound to be screened and the precursor may be above 1, below 1 or equal to 1. For example, compound to be screened may be added in excess.

The micro-organism is preferably present in amounts of $10^2$-$10^{14}$, more preferably $10^5$-$10^{12}$, most preferably $10^6$-$10^{10}$ cfu/ml.

In the event that the micro-organism is replaced by an enzyme preparation or by an isolated enzyme, the amount of enzyme to be added depends on the activity and longevity of the enzyme. Depending on these factors, the enzyme preparation may be added to provide units of enzymatic action in the range of 1-20'000'000.

The order in which the different constituents of the screening method are added to the medium of the screening method in general not decisive, unless the compound to be screened is added last and significant enzymatic activity has already led to formation of VSCs or other metabolites. Therefore, the precursor is preferably added after the compound to be screened, and more preferably the precursor is added after the compound to be screened, and after the micro-organism or enzyme. In order to mimic the underarm conditions leading to the formation of VSCs upon sweating, the precursor may be added 30 s to 2 hours after addition of the compound to be screened and the micro-organism or enzyme to the medium.

The method of screening of the present invention preferably comprises the step of incubating the comprising the precursor, a compound to be screened and a micro-organism or an enzyme at a temperature of 25-45° C., preferably 30-40° C. for 1 to 48 hours, more preferably, for 4 to 24 hours.

In a further step, the screening method comprises the step of determining the increase of the metabolites of the precursor in the medium, and/or the disappearance of the precursor.

The concentration of the metabolite substance or the precursor in the medium may be analyzed with standard analytical equipment. For example, Gas Chromatography-Mass Spectrometer (GC-MS) coupled to an Atomic Emission Detection (AED) may be employed. Accordingly, the metabolites, which may be VSCs, are preferably extracted from the medium, for example with ethyl acetate and injected on a $GC_{SPB1}$ column. In case of VSCs, the internal standard may be octanethiol, added to ethylacetate at 10 ppm with an injection volume of 1 µl, for example.

Other analytical methods may be employed. Due to the relatively low threshold perception value of VSCs, these metabolites in the medium of the method of the present invention may be conveniently evaluated by sniffing, for example.

If the precursor compound contains a fluorescent residue, which becomes fluorescent or, alternatively, which loses fluorescence upon cleavage of the precursor, the concentration or quantity of the metabolite may be determined by checking the fluorescent force of the medium after incubation.

In a further step, the screening method of the present invention comprises the step of concluding, from the ability of the compound to prevent increase of the metabolite or to prevent disappearance of the precursors, the compound's ability to prevent or suppress malodor development. Logically, the conclusion that a compound to be screened has the ability to prevent malodor development can be drawn in the event that the concentration of metabolites found in the medium after incubation is 0 or lower than the initial concentration of the precursor added to the medium, for example. Similarly, if the concentration of the precursor remains constant during the incubation of the medium of the screening method, the compound to be screened has a strong ability to prevent malodor development.

Optionally, a negative control of the screening method of the present invention may be run, which is devoid of the compound to be screened but which otherwise has the same constituents at the same concentrations and the same process steps as the screening method of the invention. From the different analytical outcome of control versus screening method the skilled person may conclude if the compound to be screened can efficiently inhibit development of malodor.

Different experimental settings or parameters may be envisaged that may have the consequence that the analytical outcome (concentration of precursor or metabolites) may have to be interpreted in different ways. However, the skilled person will adapt these settings in a way that a clear conclusion can be met upon the analytical results.

The present invention provides a method for preventing sweat malodor. Accordingly, compounds that have the ability of preventing malodor development on body surfaces may be identified with the screening method of the present invention. These compounds are capable of inhibiting the conversion of the compound of formula (I) to VSCs. For the purpose of administration or applying to body surface, a sufficient quantity of at least one compounds may then be put in a form that may be easily administrated or applied to the skin.

For example, the compound for prevention of malodor may be added to a body care product, such as a body lotion, a deodorant, an unguent, a soap, a shampoo, a fine fragrance, for example. The compound may simply be added to an aqueous solution. For example, the compound may be added to an emulsion. Depending on the solubility of the compound, the skilled person will select the suitable form of application. If the compound is hydrophilic, for example, it may be added to the aqueous phase of an emulsion, which is then applied to skin surface. If the compound is lipophilic, it will be added to the oily phase of an emulsion, or to an oil-based unguent, for example.

Preferably, the compound for prevention of malodor is added in sufficient amounts to effectively inhibiting the formation of VSCs on the body surface. The necessary concentrations in the product in which the compound depend on the efficiency of the compound and the form of the product to be administered and may thus be established by the skilled person as a function of these parameters. For example, $10^{-12}$ to $10^{-4}$ mol, preferably $10^{-11}$-$10^{-5}$ mol of the compound are administered per $cm^2$ of the body surface.

The present invention provides a method for preparing a product having the ability to reduce malodor development, comprising the step of adding to the product a compound capable of inhibiting the conversion of the compound of formula (I) to a volatile sulfur compound. The product may be selected, for example, from the body care products mentioned above. The above said related to solubility and concentration of the compound in the product equally applies to the product that has the ability to reduce malodor development. Depending on the usually quantity of administrated to the skin, the concentration is accordingly adapted to obtain sufficient efficiency. For example, if the product is a deodorant applying a film on the skin of human axillae, the compound is preferably present in concentration in the range of 0.1 to 1000 mmol/L, more preferably 1 to 500 mol/L, for example.

The present invention provides a method for metabolizing a compound of the formula (I) under controlled conditions, the method comprising the step of exposing the compound of formula (I) to a micro-organism and/or to a β-lyase. The term "controlled conditions" refers to conditions other than the natural conditions on human skin, especially of the underarm region. The term "controlled condition", in contrast, refers to conditions in which the concentration of the compound of formula (I) and/or of micro-organism and/or of the β-lyase may be determined at the discretion of the skilled person. Preferably, the term "controlled conditions" refers to conditions as found in a laboratory, and/or in manufacturing facilities, for example. The screening method as disclosed above, for example, represents a controlled condition in this sense. Preferably, the term controlled conditions refers to the fact that the compound of formula (I) is metabolized within a container comprising the compound of formula (I), and a micro-organism and/or β-lyase all of which dissolved or suspended in 5 µl to 1000 L water in determined quantities and concentrations.

The present invention further provides an aqueous liquid and/or solution comprising the precursor compound of formula (I) and 1-10, preferably 1-5, more preferably 1-2 bacterial strains in concentrations of $10^1$-$10^{13}$ cfu/ml each, or for supplementing or replacing the bacterial strains, equivalent amounts of a functional β-lyase. These are the preferred concentrations required for metabolizing the precursor compound of formula (I).

The present invention also relates to the use of compounds of formula (I) and preferably of formula (I') in screening methods, assays or research methods of body malodor development, inhibition, and/or occurrence.

EXAMPLES

In Examples 1 to 5 below the direct precursor of VSCs of sweat malodor is identified and Streptococci bacterial strains having the capacity of producing VSCs are reported. This is done by comparing HPLC analysis of fermented and unfermented sweat and by excluding the presence of the precursor postulated in the prior art by comparison of molecular masses and LC retention times, suggesting the presence of another precursor in Example 1. In Examples 2 and 3, the structure of VSCs obtained by metabolic activity of bacterial strains are identified. In Examples 4 and 5 it is tested if the proposed precursor produces the same VSCs as the precursor found in natural sweat, which is done by synthesizing the present and prior art precursors (Example 4) and exposing them to different micro-organisms, followed by analysis of the metabolites.

In Example 6, a method for screening compounds having potential malodor-inhibiting effect, due to their putative ability to convert the malodor precursor into the malodorous VSCs.

In the examples below Analytical GC is performed in a Agilent 6890 instrument coupled to Atomic Emission Detection (AED from Jass, Germany); He as carrier gas; fused-silica capillary columns OV1701, DMePeBetacdx®, 10 m×0.25 mm i.d. with 0.25 µm film (from Mega, Brechbüler A. G., Switzerland). EI-MS: Agilent 6890-GC system coupled to HP-MSD-5973 quadrupole mass spectrometer; electron energy ca. 70 eV; fragment ions m/z (rel. int. in % of the base peak, SPB-1, 30 m×0.25 mm i.d. with 0.25 µm film, all from Supelco). The retention indices (1) were determined relative to the retention time (tR) of a series of n-alkanes with linear interpolation by means of a standard GC temperature program (50° C. for 5 min, then 5° C./min to 240° C. and 20 min at 240° C.) with a precision of 0.5%. 1H—, $^{13}$C, Spectra Brucker-AMX-360 spectrometer; in CDCl$_3$; δ values in ppm downfield from Me Si (=0 ppm), J in Hz; assignments by COSY45 and HMCQ experiments.

HPLC columns were Nucleodur C18 Pyramid® 250 mm×2 mm i.d., the preparative column was a Nucleodur C18 Pyramid® 250 mm×10 mm (from Machery-Nagel, Switzerland).

HPLC-MS analyses were performed using the Agilent 1100 LC-MS system equipped with a B1312A binary pump, a G1314A UV detector and a G1946D mass spectrometer with an atmospheric-pressure chemical ionization (APCI) source. Positive and negative ion mode mass spectra (scan range 50-800 Da) were recorded simultaneously. HPLC separations were performed under the same conditions as described above.

Alternatively, Thermo Finnigan positive atmospheric pressure chemical ionization (APCI) was performed using a spray voltage of 4.5 kV, capillary temperature at 200° C., N$_2$ gas at a flow rate of 55 (Finnigan arbitrary units) with an auxilliary gas flow rate set to ESI (Finnigan arbitrary units). The solvent for elution were CH$_3$CN and water that contained 0.1% formic acid. The LC gradient started at 100% water for 5 min then increased from 0% CH$_3$CN to 50% CH$_3$CN in 30 min at a flow rate of 0.25 mL/min and in the preparative mode a flow rate of 6 mL/min was used.

The bacterial strains used in the experiments below are:
*Staphylococcus epidermidis* CNCM I-3356
*Staphylococcus haemolyticus* CNCM I-3357
*Corynebacterium xerosis* DSMZ 207 43 (corresponding to the ATCC 373) was provided by the DSMZ (Deutsche Sammlung von Mikroorganismen und Zellkulturen GmbH, Braunschweig, Germany), known as a reference strain from the literature.

Example 1

Suggestion of Malodor Precursor by Sweat Collection and Fermentation

Apocrine and eccrine secretions were collected from axillae through excessive sweating. These secretions were immediately sterilized through a double filter consisting of 1-µm membrane followed by 0.2 µm sterile filter and frozen as reported in M. Troccaz, C. Starkenmann, Y. Niclass, M. van de Waal, A. J. Clark, Chem. Biodiversity, 2004, 1, 1022-1035. A total of 250 mL of the sterile axillary sweat was lyophilized and then the solid was rediluted in distilled water and percolated through a Lobar® RP-18 SiO$_2$ column. The elution was performed with portions of 200 mL of water, then the proportion of ethanol was increased up to 100%.

A small portion of each fraction (10%) were treated with *Staphylococcus haemolyticus*. HPLC-MS (APCI$^+$ and APCI$^-$) were recorded before and after incubation. Volatiles extracted from fermented broth were injected on a polar GC column coupled to MS. It was possible from these measurements to identify a trace of 3-methyl-3-sulfanylhexan-1-ol in the fermented fraction 3 (water:ethanol=4:1) and only this fraction produced a typical onion, grapefruit, sclary sage sulfury sweaty olfactive note.

Figure 1:
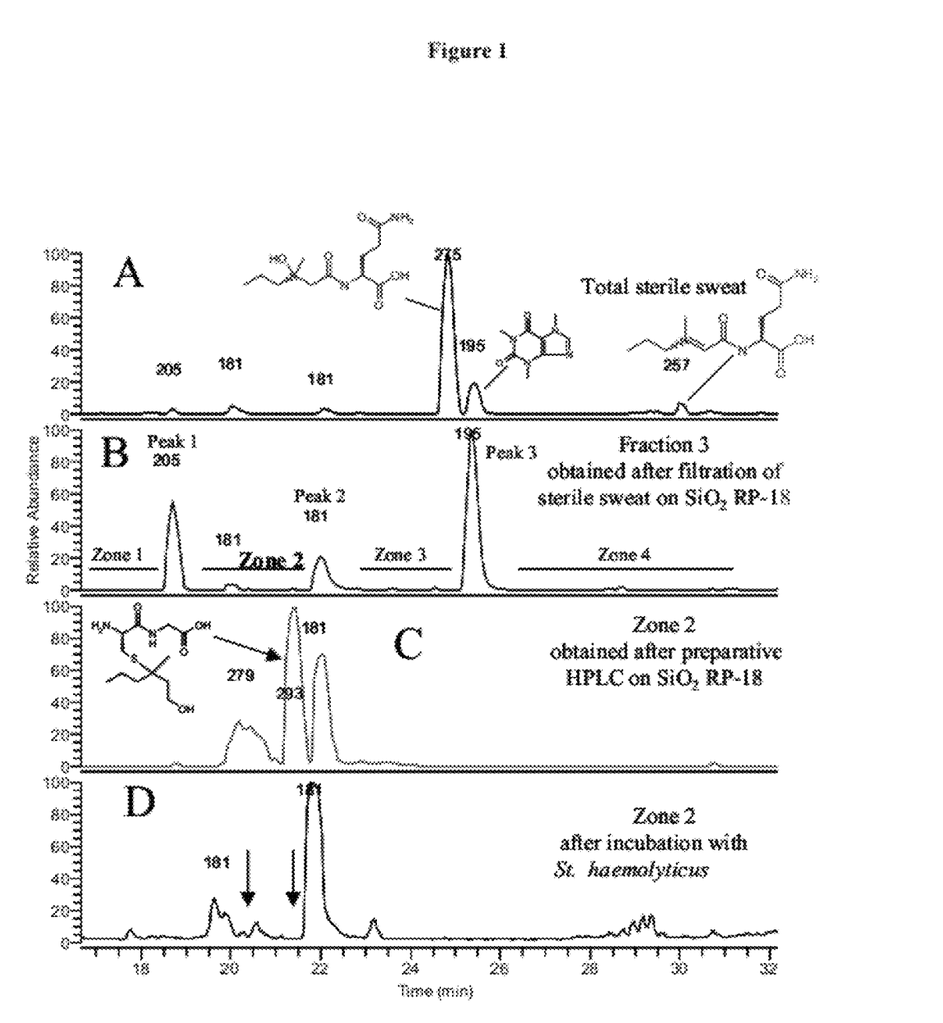
FIG. 1 shows HPLC-MS mass range (High Performance Liquid Chromatography-Mass Spectrometry Total Ion Chromatograms) obtained from sterile sweat (trace A) and different elution fractions of sweat incubated with *St. haemolyticus* (trace D) and not incubated (traces B and C). This chromatogram shows the disappearance of a putative precursor compound having a molecular mass of 293 following incubation.

A preparative separation on HPLC of fraction 3 was performed. The three major peaks were collected as well as for elutions zones between peaks (FIG. 1, trace B). Then the fraction of "zone 2" (fermented and non-fermented) was re-injected on HPLC column coupled to a APCI mass spectrometer (FIG. 1, traces C and D correspond to zone 2 of trace B).

All fractions, zones and peaks, were treated with *St. haemeolyticus* and the fraction corresponding to "zone 2" (FIG. 1, trace D) was retained because it had the typical sweat malodor smell. After incubation it was clear from the HPLC trace that M+1 corresponding to 279 and M+1 corresponding to 293 have been transformed (see arrows in FIG. 1, trace D). All injections were performed in MS-3 mode in positive and negative mode. The major compound at M+1 293 showed m/z 276, loss of NH3, then m/z 179, interpreted as a loss of 3-methylhexanol, then m/z of 162, 144, 166 attributed to loss of NH3, H2O and CO. In negative mode, M−1 291 was fragmented at m/z 143 corresponding to a β-elimination of 3-methyl-3-sulfanylhexan-1-ol.

Figure 3:
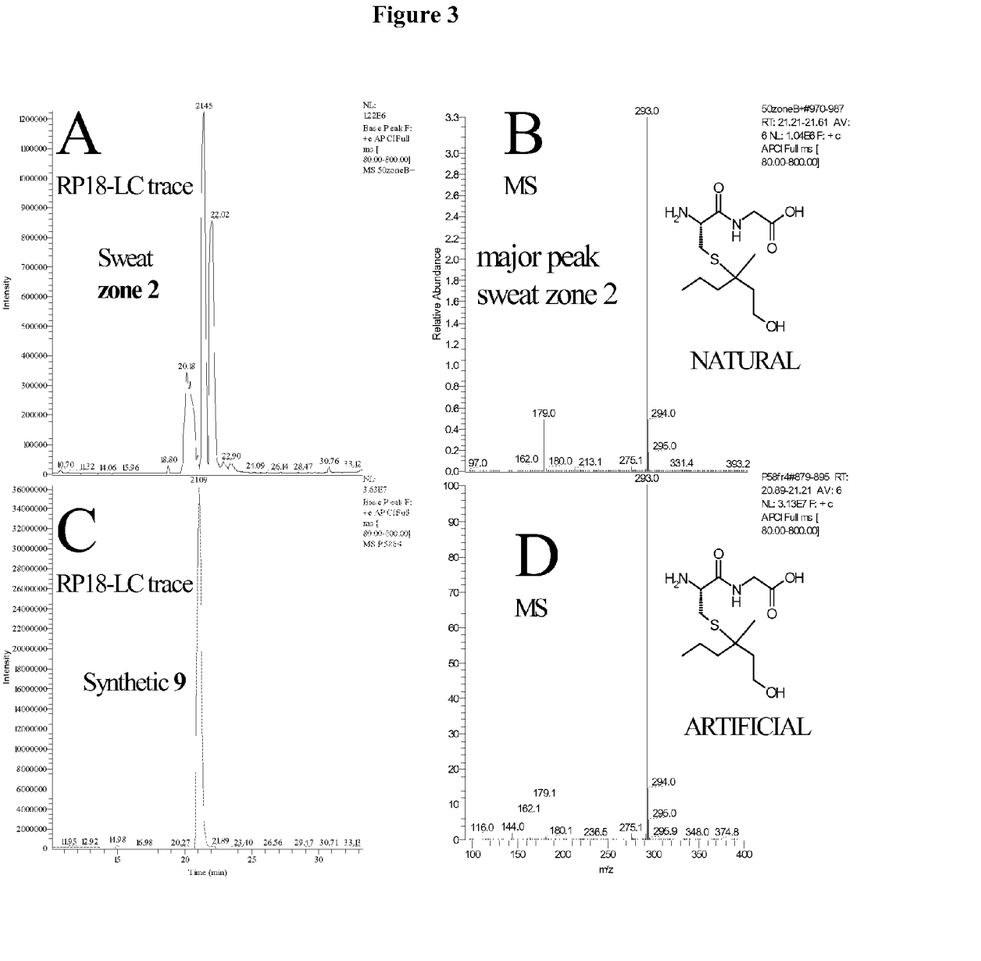
FIG. 3 shows chromatograms and mass specters obtained by LC-MS of the precursor found in "zone 2" of natural sterile sweat (A, B), and of the synthesized precursor 9 (CD).
Figure 4:
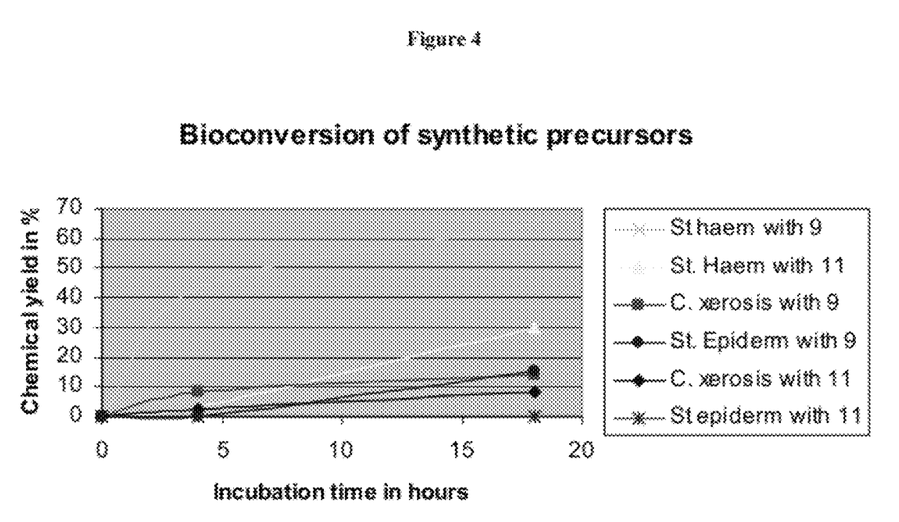
FIG. 4 shows the bioconversion of synthetic precursor compounds 9 and 10 of malodorous VSCs by bacterial strains of *St. haemolyticus*, *St. epidermidis* and *C. xerosis*. It can be seen that the precursor of the present invention (9) has been efficiently converted by all strains.
Figure 5:
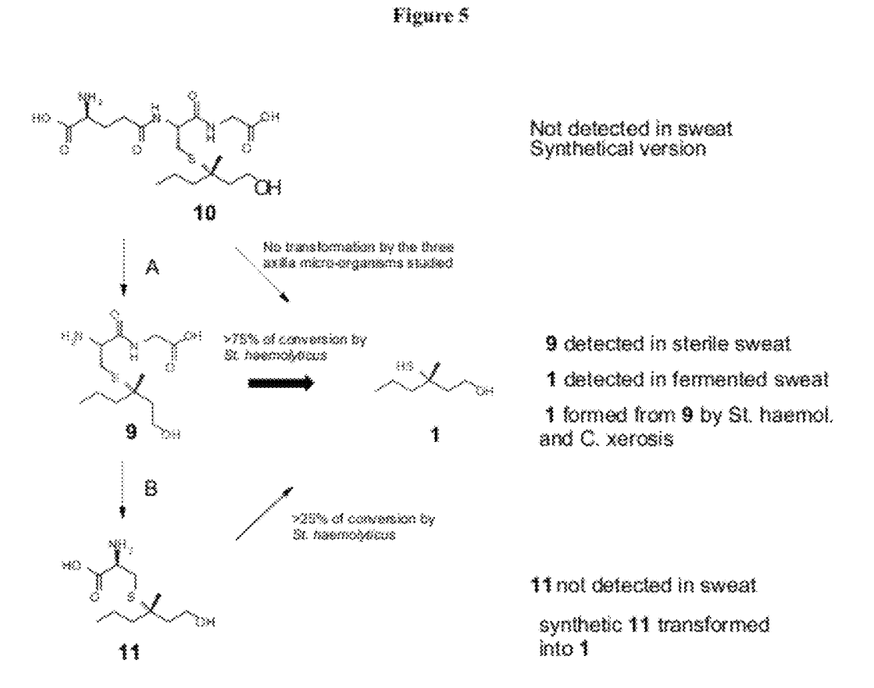
FIG. 5 shows the summary of synthetic pathways to a major VSC (1) from sterile sweat precursors. Compound (9) is an embodiment of the precursor to be used in the screening method of the present invention.

From these observations it was possible to exclude the S-conjugated glutathione (M+1 422) or the S-conjugated cysteine (M+1 236) to be precursors of 3-methyl-3-sulfanylhexan-1-ol, but S-conjugated cysteine-glycine, of molecular formula C$_{12}$H$_{24}$N$_2$O$_4$S, which correspond to a molecular weight of 292, was therefore proposed to be the precursor of 3-methyl-3-sulfanylhexan-1-ol (see FIG. 3).

Example 2

Identification of 3-S-cys-gly-3-methyl-hexane-1-ol in fraction 3

Fraction 3 was lyophilized (16 mg) and was further purified on preparative HPLC. We collected zones between peaks and peaks separately. Each fractions and zones were injected on LCMS, extracted as described below and injected on GC-MS. Zone 2 (<0.5 mg) had three APCI+ signals: a broad signal from 19.5 to 21 min. having M+1=279 and at 21.5 min. M+1=293 followed at 22 min. M+1=181. APCI− were also recorded and MS 3 were also automatically recorded. After incubation with *St. haemolyticus* the two LC-MS signals at 20 min and 21.5 min. were gone. Zone 2 produced three sulfur compounds seen on GC-MS: 3<1%: I$_{SPB-1}$ 1080, MS: 134 (40, M+), 100 (80), 74 (98), 71 (70), 55 (65), 41 (100); 2=5%: I$_{SPB-1}$ 1093, MS: 134 (5), 100 (50), 67 (40), 57 (60), 55 (100); 1=94%: I$_{SPB-1}$ 1149, MS: 148 (4), 114 (20), 97 (70), 71 (60), 55 (100). Injection on GC$_{DMePeBetacdx}$ chiral column: 1-S (rt. 17.6 min.) 62.4%, 1-R (rt. 17.62 min.) 16.2%, 1-R/S=0.005 mg (+/−0.001), ee of S=65%. Compound 2-R (rt. 16.79 min.), 2-S (rt. 16.80 min.), 2-R/S=14.7%, S-major due to peak overlapping, not quantified. Compound 3 was nearly not seen.

Example 3

Determination of Structure of Volatile Sulfur Compounds Found in Fermented Sweat Zone 2 of fraction 3 of the fermented broth was extracted with ethylacetate and injected on a $GC_{SPB-1}$ column coupled to a MS. We observed a very small shoulder with m/z 134 at a retention index corresponding to $I_{SPB1}$ 1080 and with a fragmentation pattern close to 2-methyl-3-sulfanyl-1-pentan-1-ol. Then a larger peak with m/z 134 at with a retention index $I_{SPB-1}$ 1093, corresponding to 3-sulfanylhexane-1-ol and the major product formed having m/z 148 at $I_{SPB-1}$ 1149 and accordingly to the MS fragmentation pattern it was attributed to (R/S)-3-methyl-3-sulfanylhexan-1-ol. It was also possible to establish after an injection on a chiral column, mounted on a GC equipped with an Atomic Emission Detection (AED), that the major enantiomer formed was the S-3-methyl-3-sulfanylhexan-1-ol 5-1, with an enantiomeric excess of 60%. In the case of (R/S)-3-sulfanylhexane-1-ol it was not possible to measure precisely the enantiomeric ratio due to a bad separation of both enantiomers but the S-2 enantiomer was clearly the major isomer formed.

Therefore, 2-methyl-3-sulfanyl-1-pentan-1-ol, 3-sulfanyl-hexane-1-ol and (R/S)-3-methyl-3-sulfanylhexan-1-ol were found to be important volatile sulfur compounds of sweat metabolized by *St. haemolyticus*.

Example 4

Synthesis of Sulphanyl Derivatives and Derivatives of Cysteine Conjugates as Precursors of VSCs FIG. 2 illustrates the synthesis of various derivatives and the precursor of VSCs (Compounds 9, 10, 11). The preparation of volatile sulfur compounds has been described previously (Troccaz et al, 2004). The 1,4-addition of cysteine to α,β-unsaturated aldehydes was performed by the addition of t-butoxycarbonyl (Boc)-L-cysteine to 3-methyl-2-hexenal followed by reduction with NaBH4 (Natsch et at 2004) (step a). S-Cys-conjugate 11 was obtained after deprotection of compound 6 with TFA (trifluoroacetic acid in CH2Cl2 (step b). The coupling of H-Gly-OBz to 6 (step b) was performed in CH2Cl2 in presence of PyBOP (Benzotriazol-1-yl-oxytripyr-rolidinophosphonium hexafluorophosphate) and DIPEA (diisopropylamine), in standard conditions for peptide synthesis, to prepare 7. The α-amino-protecting group of 7 was removed in CH2Cl2 and (TFA) conditions (step c) to produce 8. It was not possible to remove the benzoyl protective group by hydrogenolyse, but it was possible to perform a saponification in water, ethanol and sodium hydroxide 2% (step d) to prepare 9. The most likely precursor of volatile sulfur compounds are glutathion conjugates. For this reason 8 was coupled to Boc-Glu-OBz as described for 7, α-amino groups were cleaved in CH2Cl2, TFA conditions and the benzyl esters were hydrolyzed in aqueous sodium hydroxide and ethanol to give 10 (step e).

The exact protocol for the preparation of compound 9 is given below: (2R)—S-[1-(2-hydroxyethyl)-1-methylbutyl]-tBoc-Cys (6), prepared according to Natsch et at (2004), (679 mg, 2 mmole) was diluted in $CH_2Cl_2$ (6 ml) and H-Gly-OBzl (741 mg, 2.2 mmole), Pybop (1.14 g, 2.2 mmole) in presence of diisopropylethylamine (774 mg, 6 mmole) were stirred over night at room temperature. Usual work-up was followed by the deprotection of the α-amino group of (2R)—S-[1-(2-hydroxyethyl)-1-methylbutyl]-tBoc-Cys-Gly-OBzl 7 in $CH_2Cl_2$ (6 ml) trifluoroacetic acid (9 mL) during 1.3 hours at room temperature. The crude oily product 8 (1 g) was diluted in water (70 mL) MeOH 50 mL and NaOH (2 g) and heated 1 hour at 60° C. The pH is then brought to 4 with HCl 1M. The methanol was removed under vacuum, and the mixture was lyophilized. The solid was redilute in water (1 mL) and flash chromatographied on $SiO_2$—RP18 (column of i. d. 5 cm, high of silica 12 cm). The elution started with water and the product 9 was eluted with water ethanol in 4 to 1 ratio. We obtained 9 (340 mg, yield 58%). HPLC, r.t. 22.2 min. APCI+: M+1=293, MS2 276, MS3 179, MS4 162, MS5 144, MS6 116, APCI−: M−1=291, MS2 143, MS3 99, 58. $^1$H-NMR in $D_2O$: 4.16-4.19 (m, 1H, C(4)); 3.95 (d, J=17.5 Hz, 1H, C(2)); 3.74 (t, J=7 Hz, 2H, C(8)); 3.70 (d, J=17.5 Hz, 1H, C(2)); 3.09 (dd, J=13.5, 5.5 Hz, 1H, C(5)); 2.99 (dd, J=13.5, 8.0 Hz, 1H, C(5)); 1.83 (t, J=6.5 Hz, 2H, C(7)); 1.50-1.55 (m, 2H, C(9)); 1.38 (m, 2H, C(10)); 1.29 (s, 3H, C(12)); 0.95 (t, J=7 Hz, 3H, C(11)). $^{13}$C-NMR: 178.8 (s, C(1)); 171.0 (s, C(3)); 61.1 (t, C(8)); 55.8 (d, C(4)); 51.9 (s, C(6)); 46.2 (t, C(2)); 44.8 (t, C(9)); 43.7 (t, C(7)); 30.6 (t, C(5)); 28.3 (q, C(12)), 19.9 (t, C(10)); 16.5 (q, C(11)).

Example 5

Production of (R/S)-3-methyl-3-sulfanyl-hexane-1-ol from exposing synthesized Precursors to *St. haemolyticus*, *C. xerosis* and *St. epidermidis*

The inventors have showed above that of biodegradation of sterile sweat with different micro-organisms, *St. haemolyticus* produced the most typical sulfury, sweat odor, in spite of the prior art statement that *Staphylococci* and specifically *St. epidermidis* did not have a β-lyase activity and only *Corynebacterium* spp. were able to release thiols from S-conjugated cysteine (Natsch et al. (2004)). Surprisingly, in the present experiments, *C. xerosis* produced a weaker sulfury type odor compared to *St. haemolyticus* and we were interested to see the differences between these three strains, when they are incubated with precursors 9, 10, or 11, wherein precursor 9 is an embodiment of the compound of formula (I) of the present invention.

Bacteria isolates grown aerobically (5 mL, $8 \times 10^8$ cfu/mL), were incubated with 0.1 mg of each precursors at 35° C., over a period of 18 hours. The volatile sulfur compounds are extracted with EtOAc and analyzed on GC-AED on a chiral column. Each bio-conversion were repeated at least three times, one blank contained only the bacterium, and the other blank was made of the growing medium with the precursor alone. No sulfur compound was detected in these controls. Octane thiol was used as an internal standard, calibrations curves showed that the best reproducibility was in the range of 1 to 10 ppm, when 1 μL was injected, with less than 5% of variability. The variations of the concentration observed for 1 was correlated to the variation of the concentration of micro-organisms in the 5 mL used for the incubation but all or results were consistent; 9 gave always a better chemical yield compared to 11. Precursors were prepared from natural optically active amino-acids. The Michael type of addition of Boc-cysteine to E/Z-3 methyl-2-hexenal was not stereoselective and for this reason we expected to produce a racemic mixture of 1 from 9 with *St. heamolyticus* which was confirmed. The derivative 10 never produced any trace of 1.

The detailed fermentation protocol is given below:
Bacteria isolates were grown aerobically in the appropriate liquid media at 37° C. until $OD_{600}$=1.0. Cells were harvested by centrifugation at 3000 g, 10 min, washed once with sterile 0.1M phosphate buffer (pH 6.0) and resuspended in fresh buffer. The concentration of individual strains incubated with the sweat precursor was between $1.10^{+8}$ and $1.10^{+10}$ cfu/mL. These freshly prepared bacteria (5 mL), were incubated with 0.1 mL of precursors (5 mg in 10 mL water), (or the sweat fraction, in Example 1 above), at 37° C. pH 6 in a close bottle. After the incubation time 1, 4 and 18 hours, 1 mL of ethyl acetate containing octanethiol and octadecane at 0.02 mg/mL was added and the fermentation broth was centrifuged at 16'000 g. The organic phase was directly injected on a $GC_{SPB1}$ column coupled to MS and on a $GC_{DMePeBetacdx}$ chiral column coupled to AED detection. These experiments were repeated three times, two blanks were done with the micro-organism without the precursor and one with the precursor in the growing buffer only. No formation of sulfur compound was detected in blanks. The response factor for 1 μL injected of a solution 0.01 mg/mL of octanethiol was calculated in comparison of 1 μL injected of a racemic solution of 0.01 mg/mL of 3-methyl-3-sulphanylhexane-1-ol. The addition of both peaks areas (R/S) gave 280 (+/−5) and octanethiol 303 (+/−3) peaks surface over for injections so we used as an approximation a response factor of 1. Correlation factor for 1 μL injected on both column, were above 0.998 in the range of 1 to 10 ppm of (R/S)-3-methyl-3-sulfanylhexane-1-ol.

These results show that compound 9, which is a preferred embodiment of the compound of formula (I), is more efficiently converted into the malodorous compound 1, and is thus the likely precursor. Compound 11, however, which has been suggested in the prior art as potential precursor, gave clearly lower yield of 1, even in C. spp, which was hitherto considered to be the only micro-organism releasing VSCs. Therefore, compound 11 can not be considered to be the direct precursor in the main synthetic pathway of 1.

Example 6

Screening Potentially Malodor-Inhibiting Compounds by the Method of the Invention The inhibitive effect of β-Cl-ala-gly on the formation of malodor is assessed in this example.

Micro-organisms suspended in fresh buffer (Example 5, detailed fermentation protocol) were split in two samples X and Y (negative control) of 5 mL.

A compound to be screened of the formula

•β-Cl-ala-gly)

(obtained in Example 9) was added to sample X at a concentration of 2 μmol/L.

The samples comprising suspended micro-organisms and the compound to be screened were incubated at 37° C. for 30 min.

Thereafter, both samples were further incubated with 0.1 mL of the precursor (2R)—S-[1-(2-hydroxyethyl)-1-methylbutyl]-Cys-Gly (5 mg in 10 mL water) (obtained in Example 4), at 37° C. pH 6 in a close bottle. This corresponds to a total of 2 μmol/L of precursor on both samples.

The concentration of individual strains incubated with the malodor precursor is typically between $1.1×10^8$ and $1.1×10^{10}$ cfu/mL.

After the incubation times of 1, 4 and 18 hours, the increase of malodorous substance (compound 1 in FIG. 2) is briefly determined by sniffing of a trained person.

If β-Cl-ala-gly has the ability to prevent or suppress malodor development, it will exhibit less or no pungent taste typical for compound 1 in FIG. 2 (see Example 1).

In addition, a quantitative analysis of sulfur compounds in the fermented medium is performed in order to determine the efficacy of β-Cl-ala-gly's in preventing malodor development.

Accordingly, 1 mL of ethyl acetate containing octanethiol and octadecane at 0.02 mg/mL are added to samples (X) and (Y) followed by centrifugation at 16'000 g. The organic phase was directly injected on a GC SPB1 column coupled to MS and on a GC DMePeBetacdx chiral column coupled to AED detection.

For the internal standard, the response factor for 1 μL injected of a solution 0.01 mg/mL of octanethiol was calculated in comparison of 1 μL injected of a racemic solution of 0.01 mg/mL of 3-methyl-3-sulphanylhexane-1-ol. The addition of both peaks areas (R/S) gave 280 (+/−5) and octanethiol 303 (+/−3) for peaks surface over injections, so we used as an approximation a response factor of 1. For sample (X), the correlation factor for 1 uL injected on both columns, were above 0.998 in the range of 1 to 10 ppm of (R/S)-3-methyl-3-sulfanylhexane-1-ol.

Stoichiometrically, 0.2 μmol of precursor produces 0.025 mg of VSC in 1 ml ethylacetate, if all precursor is metabolized. If less than 0.25 mg of VSC is measured in sample X by the AED system, the screened compound, β-Cl-ala-gly, has the ability to reduce the development of malodor. In other words, not all of the precursor is metabolized. The more VSC is found in sample X, which also contains a putative inhibitor, the less the compound has inhibitive properties. The method of the present invention permits effectively to screen for compounds on their ability to prevent, suppress or treat malodor development on body surfaces.

Example 7

Synthesis of N-{[(4R)-4-amino-4,5-dihydro-2-thienyl]carbonyl}glycine (compound IIIa)

Step 1: Preparation of ethyl N-(tert-butoxycarbonyl)-S-(2-ethoxy-2-oxoethyl)-L-cysteinate 12

To L-cysteine ethyl ester hydrochloride ACROS (13.5 g, 72.8 mmole), CH2Cl2 128 mL and di-tert-butyldicarbonate (16.9 g, 77.5 mmole) were added at 0° C. drop wise, followed by triethyl amine (39 mL, 279 mmole). The ice bath was removed and the reaction was stirred 5 hours. Ethylbromoacetate, (10.5 mL, 94.6 mmole) was added at 0° C. After 30 min. the ice bath was removed and the reaction was stirred 1 hour at room temperature. The CH2Cl2 was distilled off; the reaction mixture was rediluted with brine and extracted twice with diethylether. After concentration, the crude product (25.7 g) was flash chromatographied (column diam. 7.5 cm, SiO2 15 cm high), elution with cyclohexane-ethylacetate (75/25) to give 13.76 g of (12) (yield 56%).

Step 2: Preparation of (R)-Ethyl-4-[(tert-butoxycarbonyl)amino]tetrahydro-3-oxo-2-thiophenecarboxylate 13

NaH (1.64 g, 55%-65% Fluka, 41 mmole) washed with pentane twice, was suspended in THF (20 mL), then EtOH anhydrous (2.4 mL, 41 mmole) was added slowly. When the production of $H_2$ stopped, more THF (160 mL) was added and followed by 12 (13.73 g, 41 mmole) in THF (20 mL). After 40 min. acetic acid 4 mL was added. The solvent was removed under vacuum. The crude product was extracted with diethylether and washed with brine. Crude (12 g) was flash chromatographied (column diam. 7.5 cm, SiO2 15 cm high), elution with cyclohexane-ethylacetate (4/1) to give 9.22 g of 13 (yield 78%).

Step 3: Preparation of (R)-4-[(tert-butoxycarbonyl) amino]-4,5-dihydro-2-thiophenecarboxylic acid 14

3.1: Reduction

The oxo-ester (13) (9.16 g, 31.7 mmole) in EtOH 90 mL was reduced with NaBH4 (844 mg, 22 mmole) added portion wise at −30° C. After 30 min at −30° C., acetone 8.7 mL followed with acetic acid 1.1 mL were added. The crude mixture was concentrated at 40° C. under 100 mbar, extracted with EtOAc and brine to pH 7. The solvent was removed under 0.1 mbar, crude 9.20 g (yield 99%) of (R)-ethyl-4-[(tert-butoxycarbonyl)amino]tetrahydro-3-hydroxy-2-thiophenecarboxylate.

3.2: Elimination

The hydroxy-ester (9.15 g, 31 mmole) was diluted in CH2Cl2 130 mL, in presence of triethylamine 17.5 mL. At 0° C. mesylchloride (4.88 mL, 62.9 mmole) was added drop wise. After 4 hours stirring CH2Cl2 was added, and the organic phases were extracted to neutrality with brine. The solvent was evaporated and the crude product (9.12 g) was flash chromatographied (column diam. 7.5 cm, SiO2 15 cm high) elution with cyclohexane-ethylacetate (85/15) to give 6.5 g (yield 77%) of (R)-ethyl-4-[(tert-butoxycarbonyl) amino]-4,5-dihydro-2-thiophenecarboxylate 3.3: Saponification The ester (6.5 g, 23.8 mmole) was saponified in solution in EtOH 76 mL. At 0° C., an aqueous solution of LiOH 1N 32 mL, was added slowly and the reaction was then stirred 2 hours at room temperature. HCl 3 N was added, the EtOH was removed under vacuum, then the product was extracted with $Et_2O$, crude 5.93 g of a brown powder (14).

Step 4: Preparation of Compound (IIIa)

4.1: Coupling

The N-boc protected carboxylic acid (14) (2.45 g, 10 mmole) in solution in $CH_2Cl_2$ 30 mL was treated with H-Gly-OBzl-p-tosylate (3.7 g, 11 mmole, Novabiochem) and diisopropylethylamine (3.88 g, 30 mmole) 16 hours at room temperature. The mixture was extracted with $CH_2Cl_2$ and washed with brine. The crude product 11 g, was flash chromatographied (column diameter 7.5 cm, 15 cm high SiO2) elution with EtOAc, to give 3.66 g of a whit solid (yield 93%) of benzyl N-({(4R)-4-[(tert-butoxycarbonyl)amino]-4,5-dihydro-2-thienyl}carbonyl)glycinate 4.2: Deprotections The protected compound (3.60 g, 9.18 mmole) in solution in $CH_2Cl_2$ 12 mL was treated with TFA 26 mL 4 hours at room temperature. TFA was distilled off in azeotropic mode by adding 3 portions of toluene (3×80 mL). The crude product (3.11 g) was directly dissolved in water 55 mL, methanol 55 mL, sodium hydroxide 2.2 g and stirred at room temperature 2 hours. Then the reaction was cooled at 0° C. and HCl 3 M was added to pH 1. The resulting mixture was concentrated at 10 mbar, 30° C. and chromatographied (column 2.5 cm, 80 g Dowex 50WX8) same procedure described above. We obtained 1.2 g (yield 65%) of compound IIIa.

APCI+: M+1=202, $^1$H-NMR in $D_2O$: 6.37 (d, J=3.0 Hz, 1H, C(4)); 4.82-4.90 (m, 1H, C(3)); 3.88-3.80 (m, 1H, C(2)); 3.84 (s, 2H, C(7)); 3.43 (dd, J=13.0, 3.0, 1H, C(7)). $^{13}$C-NMR: 179.0 (s, C(8)); 166.3 (s, C(6)); 148.0 (s, C(5)); 125.4 (d, C(4)); 61.3 (d, C(3)); 46.4 (t, C(7)); 38.6 (t, C(2)).

Example 8

Synthesis of Inhibitor: Preparation of N-[(2S)-2-amino-4-pentynoyl]glycine (compound VI)

To H-propargyl-DL-gly-OH Bachem (25 mmole, 2.83 g) in NaOH 0.1 N 50 mL and dioxane 50 mL was added di-tbutyl dicarbonate Fluka (75 mmole, 16.35 g) during 10 min. and the pH was kept at 9.5 by addition of NaOH 1 N. After 2 hours the dioxane was removed under vacuum, the solution was acidified with HCl 1 M, extracted with ethylacetate, washed three times with $KHSO_4$ 5%, dried on $Na_2SO_4$, filtered and concentrated under vacuum. The crude mixture (25 mmole, 5.4 g) in $CH_2Cl_2$ was coupled to H-gly-Obz-p tosylate with Pybop (27 mmole, 14 g) and diidopropyl ethylamine (75 mmole, 9.67 g). Stirred 3 hours at 22° C. The crude mixture was then diluted with $CH_2Cl_2$ 700 mL and washed with brine twice. The organic phase was dried on $Na_2SO_4$, filtered and flash chromatographied ($SiO_2$, 15 cm high, in a 7 cm diameter column), elution with ethylacetate to give 8.4 g. This crude product (23 mmole, 8.3 g) was treated with in $CH_2Cl_2$ 22 mL with TFA 50 mL. After 2 hours, TFA was removed by azeotropic distillation with benzene, three times 200 mL, to give crude 6.5 g.

Only half of this crude product (12.5 mmole, 3.25 g), was saponified with NaOH (75 mmole, 3 g), in MeOH 75 mL, and water 75 mL. After 2 hours the mixture was acidified with HCl 1 M, the solvent was remove under vacuum and the residue was flash-chromatographied ($SiO_2$—RP18, 15 cm high, column diam. 4.5 cm). The column was eluted with EtOH/water 7:3, the solvent was removed under vacuum and compound VI 1.36 g was obtained.

APCI+: M+1=171, $^1$H-NMR in $D_2O$: 4.33-4.28 (m, 1H, C(2)); 4.08 (m, 2H, C(6)); 3.01-2.88 (m, 2H, C(3)); 2.61 (dd, J=2 Hz, 1H, C(5)). $^{13}$C-NMR: 175.7 (s, C(7)), 171.6 (s, C(1)); 79.2 (s, C(5)), 77.4 (d, C(5)), 54.2 (d, C(2)), 44.2 (t, C(3)); 23.9 (t, C(4)).

Example 9

Preparation of 3-Chloro-Ala-Gly (15)

Step 1: Coupling

N-Boc-β-chloro-Ala-OH Bachem (5 mmole, 1.12 g), in $CH_2Cl_2$ and H-Gly-Obz-p-tosylate Novabiochem (5.5 mmole, 1.85 g), PyBOP Novabiochem (5.5 mmole, 2.86 g), diisopropyl ethylamine (15 mmole, 1.94 g) are stirred 16 hours at 22° C. The crude mixture in then filtered on $SiO_2$, eluted with ethylacetate (50 mL) to give a crude product after concentration of 1.84 g (yield 99%).

Step 2: Deprotection

The crude product obtained (4.8 mmole, 1.8 g) was diluted in CH$_2$Cl$_2$ 9 mL and TFA 20 mL was added. The mixture was stirred 3 hours at 22° C. and purified by azeotropic distillation with benzene (3×100 mL) under high vacuum. The crude product (5 mmole, 1.7 g) was diluted in water 10 mL plus ethanol 20 mL and hydrogenated with H2 in presence of a catalytic amount of Pd 5% on active carbon. After 16 hours the mixture was filtered on celite, rinsed twice with water. The ethanol was removed under vacuum and the crude product was chromatographied on Dowex 50WX8 (column 2.5 cm. diam., 80 g). It was loaded in 5 mL of water, the column was rinsed with 150 mL of water. The elution was made with successively 100 ml portions of NH$_4$OH 0.4 M, 0.8 M, 1.2 M, 1.6 M, 2.0 M. The elution was followed by HP-TLC (SiO$_2$, Merck 1.05628.0001), mobile phase AcOH/tBuOH/H$_2$O/AcOH 2/1/1/1. Compound 15 was eluted with 1.6 M ammonia and after concentration, 730 mg of 15 was obtained (yield 81%).

APCI+: M+1=181, $^1$H-NMR in D$_2$O: 4.53-4.51 (m, 1H, C(2)); 4.16-4.02 (m, 2H, C(3)); 4.03 (d, J=8 Hz, 1H, C(4)); 3.98 (d, J=8 Hz, 1H, C(4)). $^{13}$C-NMR: 176.7 (s, C(5)), 169.9 (s, C(1)); 56.8 (d, C(2)), 45.4 (t, C(3)); 44.9 (t, C(4)).

Example 10

Preparation of N-[3-amino-benzoyl]glycine (compound VII)

To 3-aminobenzoic acid 11 ABCR (6.85 g, 50 mmole) in CH$_2$Cl$_2$ 90 mL was added ditert-butyldicarbonate (11.66 g, 53.3 mmole) and at 0° C., triethylamine (27 mL, 193 mmole) drop wise. After 4 hours stirring at 22° C., water was added and the N-boc-ortho-aminobenzoic acid was extracted with CH$_2$Cl$_2$ to give crude, after concentration 11.94 g. To the crude product (5.93 g, 25 mmole) in CH$_2$Cl$_2$ 75 mL was added, H-Gly-Obz p-tosylaste Novabiochem (14.3 g, 27.5 mmole), PyBOP (14.3 g, 27.5 mmole) and diisopropylethylamine (9.67 g, 75 mmole). This mixture was stirred over night, then rediluted in water 200 mL, extracted with CH$_2$Cl$_2$, dried on Na$_2$SO$_4$ anhydrous and concentrated. The crude product was flash chromatographied (column diam. 7.5 cm, SiO2 15 cm high) elution with cyclohexane-ethylacetate (2/3) to give 4.19 g (yield 43.6%). These (4.19 g, 10.9 mmole) were rediluted in CH$_2$Cl$_2$ 13 mL, and treated with trifluoro acetic acid 26 mL. After 3 hours, toluene was added in three portions of 50 mL and the excess of TFA was removed by azeotropic distillation under vacuum. Crude 3.57 g. Then the saponification was performed by catalytic hydrogenation with H$_2$ on Pd/C 5% in water 20 mL and ethanol 40 mL, during 15 hours at 22° C. The crude mixture was filtered on celite, concentrated under vacuum and flash chromatographied (column diam. 4.5 cm, SiO2-RP18 15 cm high) elution with water 200 mL and water ethanol 100 mL (4/1) gave 12 1.4 g (yield 54.7%).

APCI+: M+1=195, $^1$H-NMR in D$_2$O: 7.50-7.42 (m, 2H), 7.36-7.22 (m, 1H), 3.9 (s, 2H). $^{13}$C-NMR: 179.1 (s), 172.9 (s); 143 (s), 137.8 (s), 133.05 (d), 125.2 (d); 124.5 (d), 120.3 (d), 46.3 (t).

Example 11

Inhibitive Effect of Compounds IIIa, VI; Increasing Effect of Compound VII

Compounds IIIa, VI and VII were tested according to the procedure of Example 6. Compounds were added at 2 µmole, compounds IIIa and VI resulting in a 25% and 75% inhibition of production of (S)-3-methyl-3-sulfanylhexan-1-ol. These compounds are thus effective in inhibiting the production of malodorous volatile compounds from precursors present in sweat. Compound VII resulted in an increased production of (S)-3-methyl-3-sulfanylhexan-1-ol if compared to the control.

What is claimed is:

1. A method for selecting compounds having the ability to suppress or reduce malodor development on body surfaces, which comprises:
   providing a medium that includes a compound to be screened and at least one bacterial strain selected from the group consisting of family Streptococci, Corynebacteria and Bacilli, or a preparation comprising a functional β-lyase;
   adding to the medium at least one precursor compound of formula (I')

in which R$_1$ is selected from the group consisting of the compounds of formulae:

with the dotted line representing the location of the carbon bond binding to the sulphur atom and;
   determining a change in the amount of at least one metabolite of the precursor compound or the presence of the precursor compound itself to determine whether the screened compound has the ability to suppress or reduce malodor or malodor development.

2. The method of claim 1, wherein the precursor compound is added to the medium after the adding to the medium of the compound to be screened and the bacterial strain or the β-lyase.

3. The method of claim 1, wherein the compound to be screened is a compound of formula (III)

(III)

in which:

R₆ is a $C_2$-$C_{20}$ alkyl, alkenyl, alkynyl or aryl group, optionally substituted and optionally comprising one or more heteroatoms, and, the dotted line represents a double bond, in case of which Z is selected from the group consisting of $CR_7$ and N, or, the dotted line represents a single bond, in case of which Z is selected from the group consisting of $NR_7$, $CR_7R_8$, O and S, with $R_7$ and $R_8$ being, independently of each other, selected from H and $C_1$-$C_{10}$ alkyl, alkenyl and alkynyl groups.

4. A method for selecting compounds having the ability to suppress or reduce malodor development on body surfaces, which comprises:

providing a medium that includes a compound to be screened, the compound being:

(IIIa)

(VI)

adding to the medium at least one precursor compound of formula (I')

(I')

in which $R_1$ is selected from the group consisting of the compounds of formulae:

(1')

(2')

(3')

(12')

and (13')

with the dotted line representing the location of the carbon bond binding to the sulphur atom and;

determining a change in the amount of at least one metabolite of the precursor compound or the presence of the precursor compound itself to determine whether the screened compound has the ability to suppress or reduce malodor or malodor development.

5. The method of claim 1 which further comprises applying the selected compound to a body surface to suppress or reduce malodor or malodor development.

6. The method of claim 5, wherein the selected compound is applied to axillary skin.

7. The method of claim 5, wherein the selected compound to be applied inhibits the conversion of the compound of formula (I') to a volatile sulfur compound.

8. The method of claim 5, which further comprises adding the selected compound to a product that is applied to the body surface.

9. The method of claim 6, wherein the selected compound is exposed to both the micro-organisms *Staphylococcus haemolyticus* having deposit number CNCM I-3356 and *St. epidermidis* having deposit number CNCM I-3357.

10. A method for selecting compounds having the ability to suppress or reduce malodor development on body surfaces, which comprises:

providing a medium that includes a compound to be screened and the micro-organisms *Staphylococcus haemolyticus* having deposit number CNCM 1-3356 and *St. epidermidis* having deposit number CNCM 1-3357;

adding to the medium at least one precursor compound of formula (I')

(I')

in which $R_1$ is selected from the group consisting of the compounds of formulae:

(1')

(2')

(3')

(12')

(13')

with the dotted line representing the location of the carbon bond binding to the sulphur atom and determining a change in the amount of at least one metabolite of the precursor compound or the presence of the precursor compound itself to determine whether the screened compound has the ability to suppress or reduce malodor or malodor development.

\* \* \* \* \*

UNITED STATES PATENT AND TRADEMARK OFFICE
CERTIFICATE OF CORRECTION

PATENT NO.         : 9,073,966 B2                                Page 1 of 1
APPLICATION NO.    : 13/483722
DATED              : July 7, 2015
INVENTOR(S)        : Starkenmann et al.

It is certified that error appears in the above-identified patent and that said Letters Patent is hereby corrected as shown below:

In the specification

Column 13:
Line 29, before "values in ppm", please delete "6" and insert -- δ --.

In the claims

Column 22:
Line 58, claim 1, line 20, after "bond binding to the sulphur", delete "atom and;" and insert
-- atom; and --.

Column 24:
Line 22, claim 4, line 20, after "bond binding to the sulphur", delete "atom and;" and insert
-- atom; and --.
Line 49, claim 10, line 6, delete "1-3356" and insert -- I-3356 --.
Line 51, claim 10, line 8, delete "1-3357" and insert -- I-3357 --.

Column 25:
Line 26, claim 10, line 20, after "bond binding to the sulphur", delete "atom and" and insert
-- atom; and --.

Signed and Sealed this
Twenty-seventh Day of October, 2015

Michelle K. Lee
*Director of the United States Patent and Trademark Office*